US006798222B2

United States Patent
Tanaka et al.

(10) Patent No.: US 6,798,222 B2
(45) Date of Patent: Sep. 28, 2004

(54) MIGRATION MEASURING METHOD AND MEASURING APPARATUS

(75) Inventors: Hirokazu Tanaka, Utsunomiya (JP); Sachio Yoshihara, Utsunomiya (JP); Takashi Shirakashi, Utsunomiya (JP); Hiroaki Hiramatsu, Utsunomiya (JP); Kazuhiro Kumekawa, Tochigi (JP); Fumitaka Ueta, Yaita (JP)

(73) Assignee: Espec Corporation, Osaka (JP)

(*) Notice: Subject to any disclaimer, the term of this patent is extended or adjusted under 35 U.S.C. 154(b) by 233 days.

(21) Appl. No.: 10/206,974

(22) Filed: Jul. 30, 2002

(65) Prior Publication Data

US 2003/0160623 A1 Aug. 28, 2003

(30) Foreign Application Priority Data

Feb. 28, 2002 (JP) ........................................ 2002/053623

(51) Int. Cl.[7] ............................................... G01R 27/08
(52) U.S. Cl. ........................................ 324/715; 324/719
(58) Field of Search .................................. 324/715–719

(56) References Cited

FOREIGN PATENT DOCUMENTS

| JP | 11211684 A | * | 8/1999 | .......... G01N/27/04 |
| JP | 11211778 A | * | 8/1999 | .......... G01R/31/00 |
| JP | 2002296166 A | * | 10/2002 | .......... G01N/5/02 |

* cited by examiner

Primary Examiner—Minh H Chau
(74) Attorney, Agent, or Firm—Rader, Fishman & Grauer PLLC

(57) ABSTRACT

A migration measuring method based on an alternating current impedance method, including steps: direct current with fine alternating current superposed is applied across electrodes (1), (2) to measure the impedance there between; and a surface static capacity (c) is calculated from the measured value of impedance in order to measure migration in accordance with the variation of the calculated surface static capacity.

20 Claims, 16 Drawing Sheets

F I G . 1
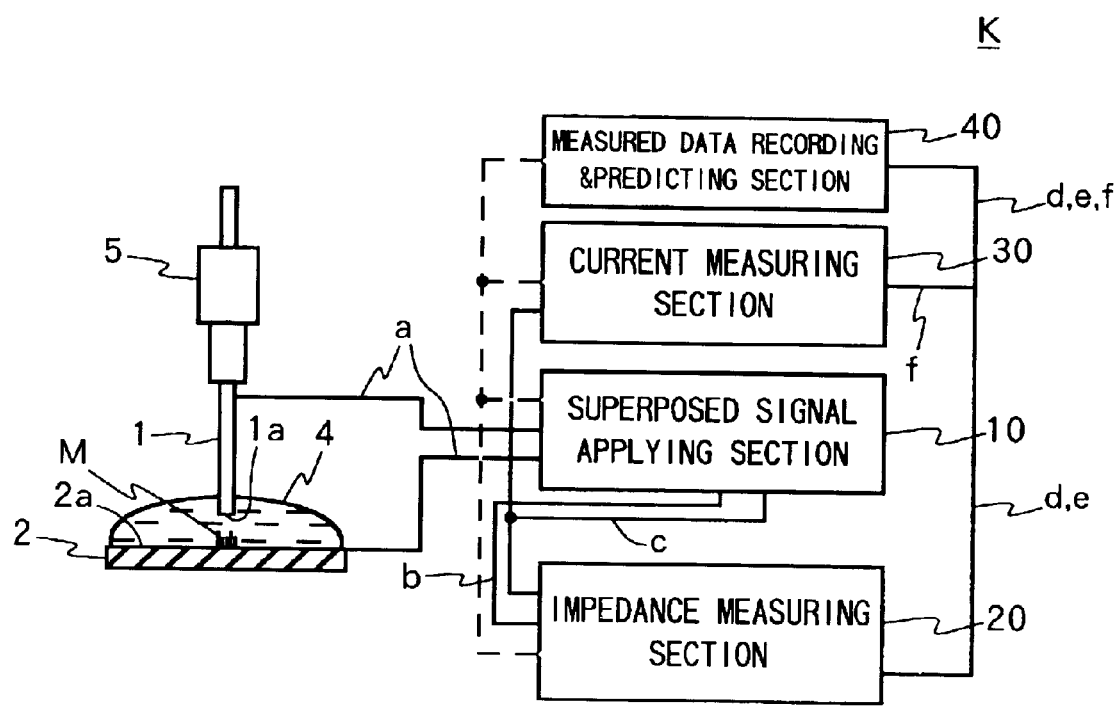

FIG. 2
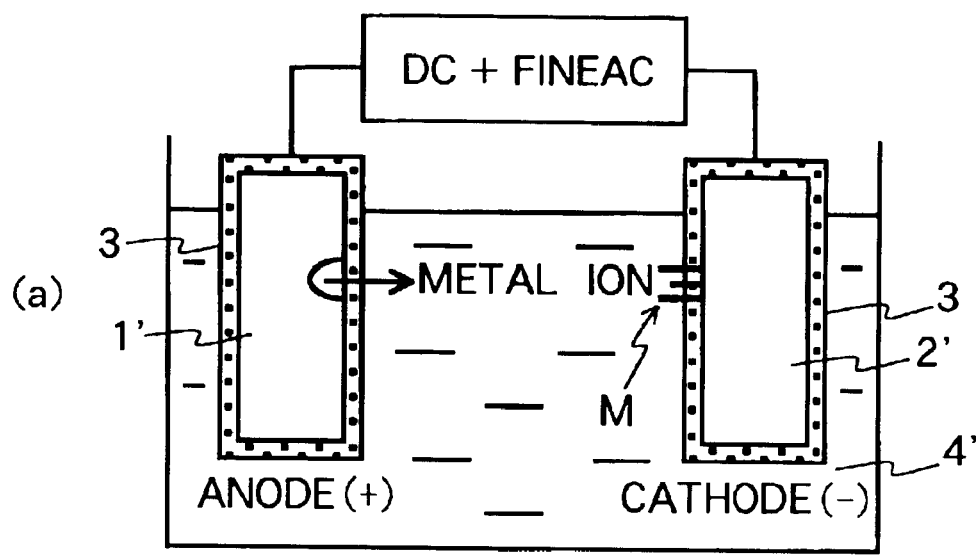
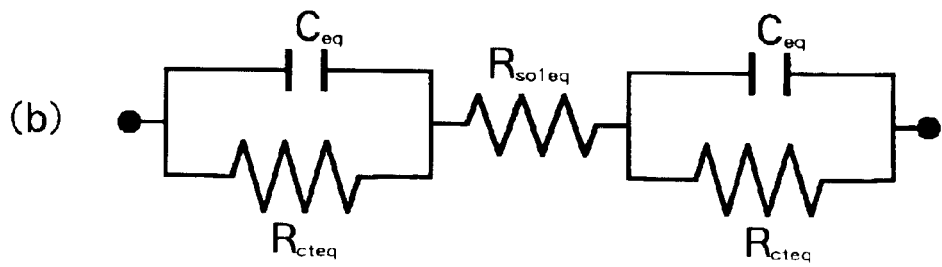

FIG. 6
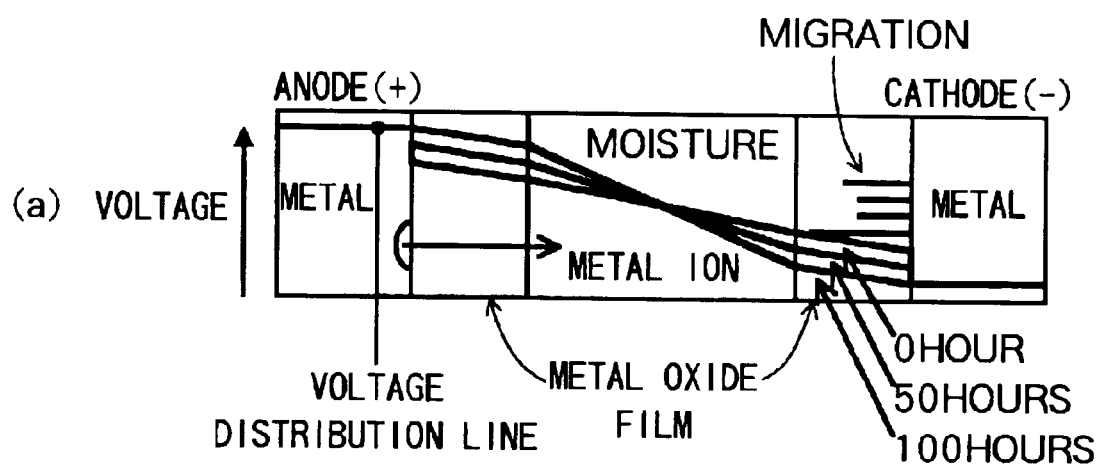
(a)
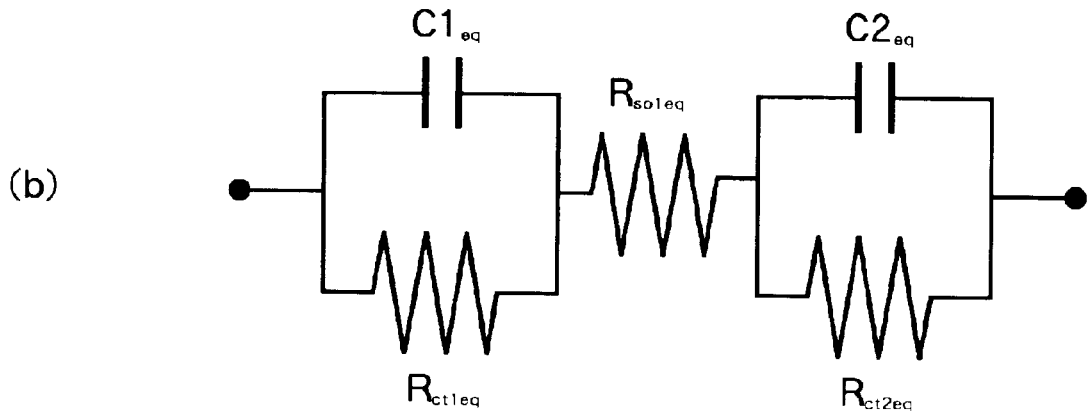
(b)

FIG. 7
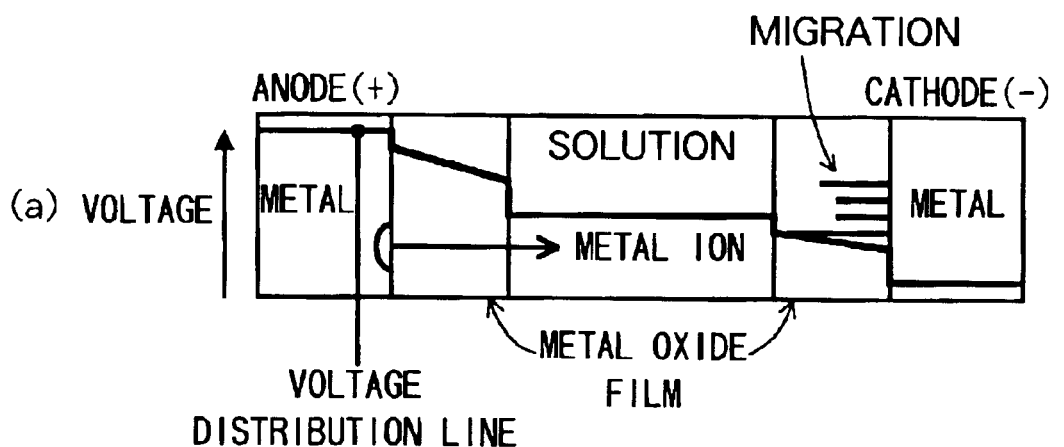
(a)
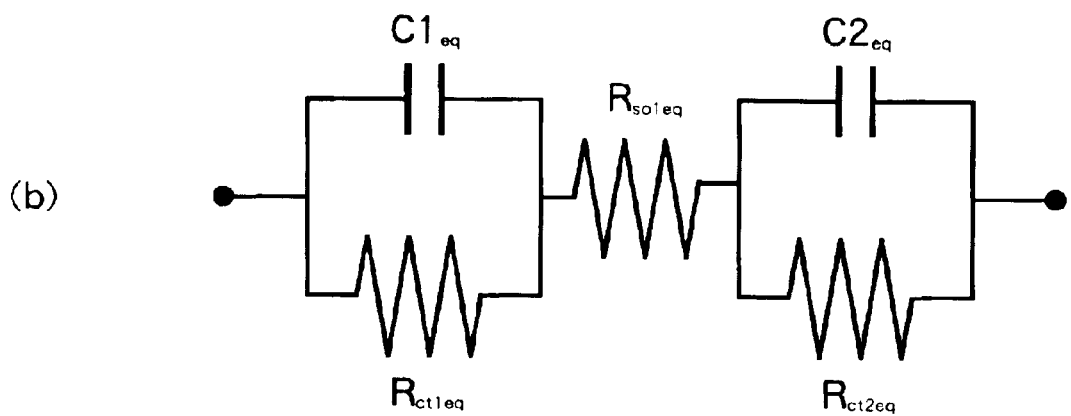
(b)

F I G . 1 3
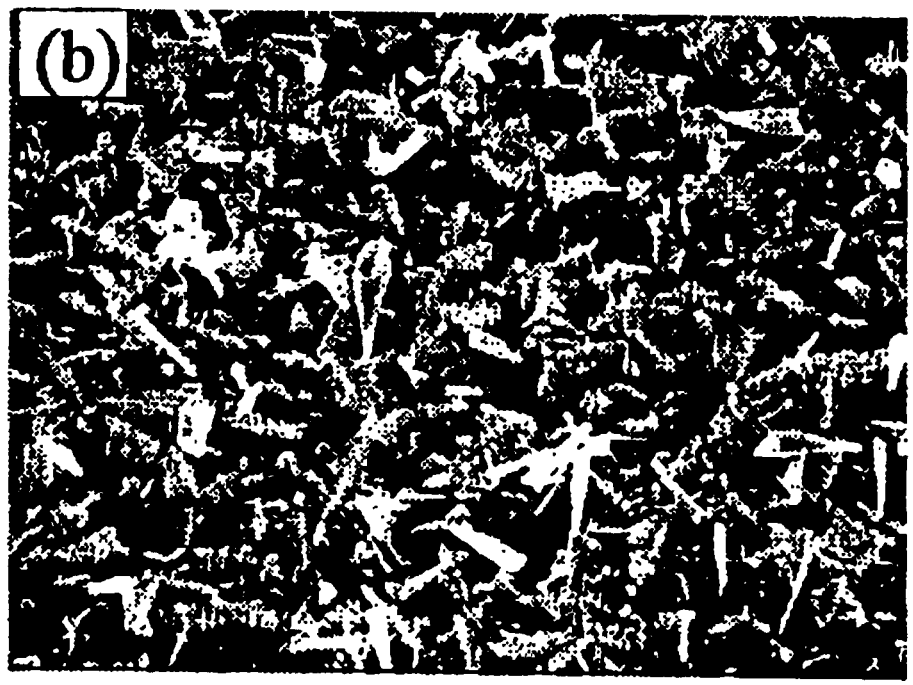

F I G . 1 4

MIGRATION MEASURING METHOD AND MEASURING APPARATUS

TECHNICAL FIELD OF THE INVENTION

The present invention relates to a migration measuring method and measuring apparatus. More particularly, the present invention relates to a migration measuring method and measuring apparatus for evaluating the resistance to insulation deterioration of materials and components of electronic equipment due to migration.

BACKGROUND ART

It is conventionally well known that when an electric field is applied onto a conductor circuit board with water sticking thereto, elution and deposition of electrode material are repeated, soon causing generation of short circuit between electrodes, that is, so-called ionic migration or electrochemical migration (hereinafter called migration) takes place. It is known that such migration is more liable to take place when the space between electrodes is narrower and is especially liable to take place in silver, copper and solder.

Accordingly, with a recent trend of circuits becoming higher in density and finer in pitch due to reduction in size and weight of electronic equipment, the influence of migration on the insulation deterioration of electronic equipment is increasingly becoming a matter of importance, and for the improvement of reliability of electronic equipment, it is now an urgent problem to make clear the basic reaction mechanism of migration and to enable the evaluation thereof.

And, a conventional migration measuring method for evaluating the migration resistance of various materials is generally such that generation of migration is observed by aiming at electrical characteristics such as change in insulation resistance due to short circuit between electrodes (for example, refer to Japanese Laid-open Patent H11-211684).

However, such conventional migration measuring method is substantially a follow-up analysis, which is not the analysis of the generation process of migration that is electrochemical phenomenon. Also, the period of measurement is very long (for example, 1,000~2,000 hours), and as a result, it causes hindrance to the purpose of shortening the product evaluation period that occupies a large portion of the period for product development.

In order to solve the problem, the inventor et al have already proposed a migration measuring method and measuring apparatus which enable the prediction of generation of migration by applying a QCM (Quartz Crystal Microbalance) method to the measurement of migration so that the process of migration can be measured in real time [Refer to November 2000: the Reliability engineering association of Japan, the 13th Reliability Symposium Announcement Reports (p27~p30), Patent Application No. 2001-095913].

FIG. 16 shows the measuring principles of the migration measuring method and measuring apparatus previously proposed by the inventor et al. In the measuring apparatus 100, an electrode (working electrode) 102 formed on the surface of crystal plate 101 and a bar electrode (counter electrode) 103 with metal-plated layer (e.g. solder-plated layer) formed thereon are arranged opposing to each other via insulating material 104 being high in hygroscopicity such as filter paper, and with ion-exchanged water 105 dripped into the gap between the electrodes 102 and 103, a predetermined DC voltage is applied thereto, then the change in the number of vibrations of the crystal plate 101 is measured, thus detecting the alteration in mass of the working electrode 102, and thereby, the quantity of metal ion deposited on the working electrode 102 is measured in real time.

However, the actual generation process of migration includes a number of elementary steps (such as charge transfer and mass transfer), and measuring the change in mass between electrodes by the QCM method is not enough to obtain the information in these elementary steps and to sufficiently make clear the generation mechanism of migration. Accordingly, it is often unable to precisely predict the period of generation of short circuit between electrodes and to achieve sufficient reliability. As a result, there arises a problem that the evaluation period cannot be effectively shortened.

The present invention is intended to solve the problems of the migration measuring method and measuring apparatus related to the proposal previously made by the inventor et al, and the main object of the invention is to provide a migration measuring method and measuring apparatus which enable more precise prediction of the generation mechanism of migration so that the generation period of migration can be more precisely predicted, and the invention is also intended to provide a short-circuit generation time predicting method and short-circuit generation time predicting apparatus for predicting short circuit between electrodes due to migration by using the data obtained by the measurement.

SUMMARY OF THE INVENTION

The first aspect of the migration measuring method of the present invention is a migration measuring method based on an alternating current impedance method, wherein direct current with fine alternating current superposed is applied across electrodes to measure impedance therebetween, and then surface static capacity is calculated from the measured value of impedance in order to measure migration in accordance with the variation of the calculated static capacity.

In the first aspect of the migration measuring method of the present invention, generation of migration is detected by detecting rapid decrease of surface static capacity after lapse of a given time since the start of impedance measurement.

The second aspect of the migration measuring method of the present invention is a migration measuring method based on an alternating current impedance method, wherein direct current with fine alternating current superposed is applied across electrodes to measure the impedance therebetween, and then charge transfer resistance is calculated from the measured value of impedance in order to measure migration in accordance with the variation of the calculated charge transfer resistance.

In the second aspect of the migration measuring method of the present invention, generation of migration is detected by detecting rapid decrease of charge transfer resistance after lapse of a given time since the start of impedance measurement.

The third aspect of the migration measuring method of the present invention is a migration measuring method based on an alternating current impedance method, wherein direct current with fine alternating current superposed is applied across electrodes to measure the impedance, and then surface static capacity and charge transfer resistance are calculated from the measured value of impedance in order to measure migration in accordance with the variation of the calculated surface static capacity and charge transfer resistance.

In the third aspect of the migration measuring method of the present invention, generation of migration is detected by detecting rapid decrease of surface static capacity and charge transfer resistance after lapse of a given time since the start of impedance measurement.

The short-circuit generation time predicting method of the present invention is a short-circuit generation time predicting method based on an alternating current impedance method for predicting the generation time of short circuit between electrodes due to migration, wherein direct current with fine alternating current superposed is applied across electrodes to measure the impedance therebetween, and then charge transfer resistance is calculated from the measured value of impedance in order to measure the generation time of short circuit due to migration in accordance with the calculated charge transfer resistance.

In the short-circuit generation time predicting method of the present invention, the short-circuit generation predicted time is calculated by the following equation when a water drop method is applied.

$$T_E = T_D + (R_{ctB}/(R_{ctB} - R_{ctD}))^{0.5} \times T_S$$

where $T_E$: short circuit generation predicted time $T_D$: time until inflection point detection $R_{ctB}$: charge transfer resistance before inflection point detection $R_{ctD}$: charge transfer resistance at inflection point detection $T_S$: measuring time interval Also, in the short-circuit generation time predicting method of the present invention, the short-circuit generation predicted time is calculated by the following equation when an environmental test method or humidity test method is applied.

$$T_E = T_D + (R_{cte}/(R_{cte} - R_{ctd}))^{0.5} \times ((R_{cte} + R_{sol})/R_{cte})^2 \times T_S$$

where $T_E$: short circuit generation predicted time $T_D$: time until inflection point detection $R_{cte}$: charge transfer resistance before inflection point detection (charge transfer resistance during stable period)

$R_{ctd}$: charge transfer resistance at inflection point detection $R_{sol}$: resistance before inflection point detection $T_S$: measuring time interval Thus, in the method of the present invention, for example, an anode is a bar-shaped electrode, and a cathode is a flat-plate electrode.

The first aspect of the migration measuring apparatus of the present invention is a migration measuring apparatus based on an alternating current impedance method, comprising a superposed signal applying section for applying direct current with fine alternating current superposed across electrodes; a current measuring section; an impedance measuring section for measuring impedance between electrodes; and a measured data recording and processing section for recording the value measured by the impedance measuring section in order to measure the migration, wherein the measured data recording and processing section calculates surface static capacity from the measured value of impedance and measures the migration in accordance with the variation of the calculated surface static capacity.

In the first aspect of the migration measuring apparatus of the present invention, the generation of migration is detected by detecting rapid decrease of surface static capacity after lapse of a given time since the start of the impedance measurement.

The second aspect of the migration measuring apparatus of the present invention is a migration measuring apparatus using an alternating current impedance method, comprising a superposed signal applying section for applying direct current with fine alternating current superposed across electrodes; a current measuring section; an impedance measuring section for measuring impedance between electrodes; and a measured data recording and processing section for recording and processing the value measured by the impedance measuring section in order to measure the migration, wherein the measured data recording and processing section calculates charge transfer resistance from the measured value of impedance and detects the generation of migration in accordance with the variation of the calculated charge transfer resistance.

In the second aspect of the migration measuring apparatus of the present invention, the measured data recording and processing section detects the generation of migration by detecting rapid decrease of charge transfer resistance after lapse of a given time since the start of the impedance measurement.

The third aspect of the migration measuring apparatus of the present invention is a migration measuring apparatus using an alternating current impedance method, comprising a superposed signal applying section for applying direct current with fine alternating current superposed across electrodes; a current measuring section; an impedance measuring section for measuring impedance between electrodes; and a measured data recording and processing section for recording and processing the value measured by the impedance measuring section in order to measure the migration, wherein the measured data recording and processing section calculates surface static capacity and charge transfer resistance from the measured value of impedance and measures the migration in accordance with the variation of the calculated surface static capacity and charge transfer resistance.

In the third aspect of the migration measuring apparatus of the present invention, the generation of migration is detected by detecting rapid decrease of surface static capacity and charge transfer resistance after lapse of a given time since the start of impedance measurement.

The short-circuit generation time predicting apparatus of the present invention is a short-circuit generation time predicting apparatus using an alternating current impedance method for predicting the generation time of short circuit between electrodes due to migration, comprising a superposed signal applying section for applying direct current with fine alternating current superposed across electrodes, a current measuring section, an impedance measuring section for measuring impedance between electrodes, and a measured data recording and predicting section for recording the value measured by said impedance measuring section and predicting the generation time of short-circuit between electrodes due to migration, wherein charge transfer resistance is calculated from the measured value of impedance, and the generation time of short circuit due to migration is predicted in accordance with the calculated charge transfer resistance.

In the short-circuit generation time predicting apparatus of the present invention, short-circuit generation predicted time is calculated by the following equation when a water drop method is applied.

$$T_E = T_D + (R_{ctB}/(R_{ctB} - R_{ctD}))^{0.5} \times T_S$$

where $T_E$: short-circuit generation predicted time $T_D$: time until inflection point detection $R_{ctB}$: charge transfer resistance before inflection point detection $R_{ctD}$: charge transfer resistance at inflection point detection $T_S$: measuring time interval Also, in the short-circuit generation time predicting apparatus of the present invention, the short-circuit generation predicted time is calculated by the following equation when an environmental test method or humidity test method is applied.

$$T_E = T_D + (R_{cte}/(R_{cte} - R_{ctd}))^{0.5} \times ((R_{cte} + R_{sol})/R_{cte})^2 \times T_S$$

where $T_F$: short-circuit generation predicted time $T_D$: time until inflection point detection $R_{cte}$: charge transfer resistance before inflection point detection (charge transfer resistance during stable period)

$R_{ctd}$: charge transfer resistance at inflection point detection $R_{sol}$: solution resistance before inflection point detection $T_S$: measuring time interval In the apparatus of the present invention, for example, an anode is a bar-shaped electrode, and a cathode is a flat-plate electrode.

Since the present invention has a configuration as described above, it is possible to accurately measure the process of migration in real time or on-line.

Also, according to the preferred embodiment of the present invention, short circuit between electrodes due to migration can be predicted, and it is possible to shorten the time required for the evaluation of migration resistance and to improve the productivity.

BRIEF DESCRIPTION OF THE DRAWINGS

FIG. 2 is a schematic diagram showing the principle of migration measurement by the measuring apparatus, and FIG. 2(a) shows a measuring circuit, and FIG. 2(b) shows an equivalent circuit thereof.

FIG. 5(a) shows the one just after start of measurement; FIG. 5(b) shows the one in the middle point of the range from start of measurement to generation of migration; FIG. 5(c) shows the one just after generation of migration; and FIG. 5(d) shows the one at generation of short circuit between electrodes.

FIG. 6 is a schematic diagram showing the principle of measurement in the migration measuring method in the second embodiment of the present invention. FIG. 6(a) shows the distribution of voltage across electrodes, and FIG. 6(b) shows an equivalent circuit.

FIG. 7 is a schematic diagram showing the principle of measurement based on a water drop method as a comparative example to the migration measuring method. FIG. 7(a) shows the distribution of voltage across electrodes, and FIG. 7(b) shows an equivalent circuit.

FIG. 8(a) shows the change with time of surface static capacity; FIG. 8(b) shows the change with time of charge transfer resistance; FIG. 8(c) shows the change with time of solution resistance; and FIG. 8(d) shows the change with time of current.

FIG. 9(a) shows the change of surface static capacity; FIG. 9(b) shows the change of charge transfer resistance; and FIG. 9(c) shows the change of current value.

FIG. 10(a) shows the change of surface static capacity; FIG. 10(b) shows the change of charge transfer resistance; and FIG. 10(c) shows the change of current value.

FIG. 11(a) shows the change of resonant frequency in the comparative examples 1 to 3, and FIG. 11(b) shows the change of charge transfer resistance in the examples 1 to 3.

FIG. 13 is a photo of a cathode surface in the first example, taken by a scanning electron microscope, showing a status before generation of short circuit between electrodes.

FIG. 14 is a photo of a cathode surface in the first example, taken by a scanning electron microscope, showing a status just after generation of short circuit between electrodes.

FIG. 16 is a diagram equivalent to FIG. 1 of a measuring apparatus related to the previous proposal of the inventor et al.

DETAILED DESCRIPTION OF THE INVENTION

The preferred embodiments of the present invention will be described in the following with reference to the attached drawings, however, the present invention is not limited only to these embodiments.

Embodiment 1

Figure 1:
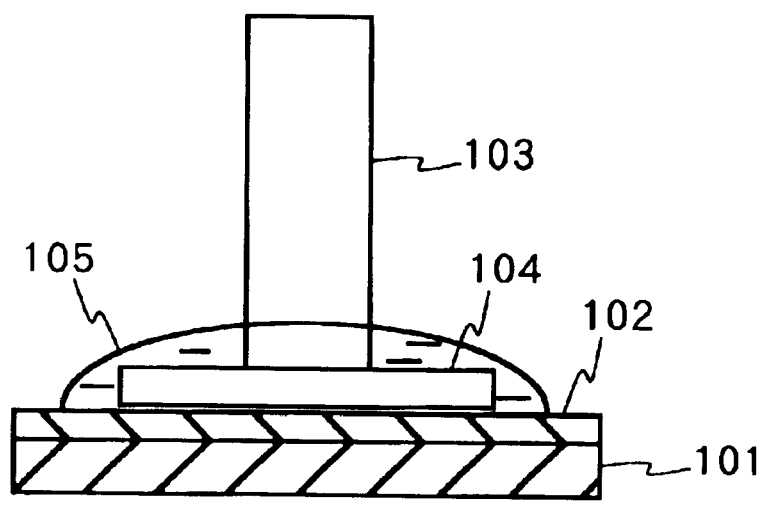
FIG. 1 is a block diagram of a measuring apparatus in the first embodiment of the present invention.

FIG. 1 is a schematic illustration of a migration measuring and short-circuit predicting apparatus (hereinafter called measuring apparatus) to which the migration measuring method in the first embodiment of the present invention is applied.

In the measuring apparatus K, a so-called alternating current impedance method is applied to the migration measurement for the evaluation of migration resistance of various metallic materials, making it possible to precisely predict the period of short circuit between electrodes (hereinafter called short-circuit) and, as a result, to shorten the time required for the evaluation of migration resistance of various metallic materials.

For the purpose of easier understanding of the migration measuring method in the first embodiment, described here is the basic principle of the migration measurement based on an alternating current impedance method with reference to FIG. 2.

In FIG. 2(a) is shown a schematic diagram of a detection circuit for detecting the electrical information used for the measurement of migration. Also, in FIG. 2(b) is shown an equivalent circuit of the detection circuit. In the figure, mark $C_{eq}$ is equivalent surface static capacity, mark $R_{cteq}$ is equivalent charge transfer resistance, and mark $R_{soleq}$ is equivalent solution resistance.

As shown in FIG. 2(a), electrodes 1', 2' with metal oxide film 3 formed on the surface are immersed in ion-exchanged water 4' (kept in steam atmosphere in the case of the environmental test method mentioned later), and in this state, direct current including fine alternating current is applied to the electrodes 1', 2', then metal ion dissolves from an anode 1', and it is deposited on the surface of a cathode 2', resulting in generation of migration M. Thus, in accordance with electrical information (about impedance) that is detectable with respect to such electrode reaction, it is possible to obtain the information (charge transfer resistance $R_{ct}$, surface static capacity C, solution resistance $R_{sol}$ mentioned later) about metal oxide film 3 that suppresses the dissolution of metal ion, and then it becomes possible to predict the period of generation by analyzing the solubility and deposition level of metal ion in various metallic materials, that is, the features of generation mechanism of migration M.

The measuring apparatus K is described in detail in the following.

The measuring apparatus K comprises, as shown in FIG. 1, a superposed signal applying section 10 for applying direct current signal a with fine sine-wave alternating current signal (hereinafter referred to as AC component) superposed (hereinafter referred to as superposed signal) to electrodes 1, 2; impedance measuring section 20 for measuring the impedance between the electrodes 1, 2 with superposed signal a applied; current measuring section 30 for measuring the current between the electrodes 1, 2; and measured data recording and predicting section 40 for recording the data of impedance and current measured by the impedance measuring section 20 and the current measuring section 30 (hereinafter referred to as measured data) and detecting the period of short circuit between electrodes due to migration M in accordance with the measured data. In case only migration is measured, it is possible to dispose a measured data recording and processing section in place of the measured data recording and predicting section 40.

As for the electrodes 1, 2, one electrode (metal dissolving side, hereinafter referred to as anode) 1 is, for example, round-bar-shaped, and the other electrode (metal depositing side, hereinafter referred to as cathode) 2 is, for example, flat-plate-shaped, on each surface of which is formed a metal layer (not shown) having a predetermined thickness subjected to the evaluation of migration.

The anode 1 is supported via micrometer 5 above the cathode 2 so as to be vertically positioned in its lengthwise direction, and in this way, the gap between electrodes 1, 2 can be adjusted so that the tip portion of the anode 1 is immersed in ion-exchanged water 4 dropped onto the surface of cathode 2.

Figure 3:
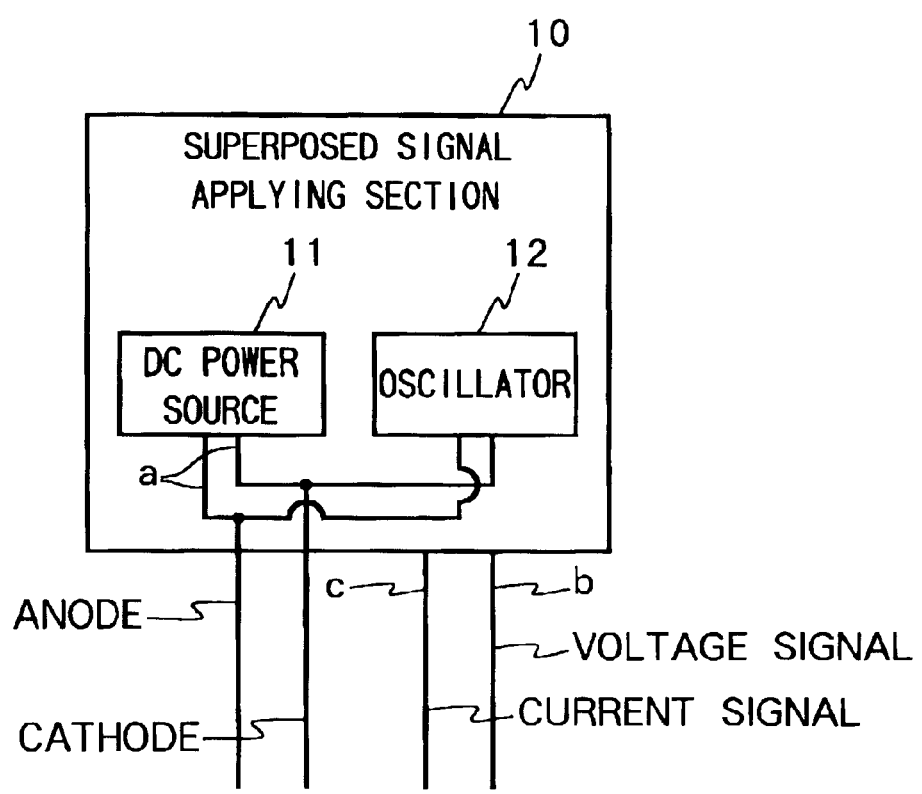
FIG. 3 is a block diagram showing the detail of a superposed signal applying section of the measuring apparatus.

Next, superposed signal applying section 10 is described with reference to FIG. 3. As shown in the figure, the superposed signal applying section 10 comprises DC power source [e.g. potentiostat (constant-potential electrolyzer)] 11 and oscillator 12.

The DC power source 11 outputs the direct current component (e. g. direct current of 1.5V) of superposed signal a. Also, it is possible to use any type of DC power source provided that it is a stable power source capable of varying output signals by external order like a potentiostat.

The oscillator 12 outputs the alternating current component (e. g. alternating current of 10 mV~50 mV, 0.1 Hz~100 KHz) of superposed signal a. Also, as the oscillator 12, in an actual equipment configuration, it is possible to use an oscillator usually installed in an impedance meter used as impedance measuring section 20 mentioned later.

The impedance measuring section 20 is, for example, a phase difference meter, which is connected to the superposed signal applying section 10, and detects voltage signal b representing the voltage and current signal c representing the current of superposed signal a output by the superposed signal applying section 10, and measures real number impedance and imaginary number impedance.

Also, the impedance measuring section 20 outputs real number impedance measured data d and imaginary number impedance measured data e, representing the result of measurement of each impedance, to the measured data recording and predicting section 40. Also, it is possible to use a so-called impedance meter as the impedance measuring section 20.

The current measuring section 30 is connected to the superposed signal applying section 10, and measures the current flowing between the electrodes 1, 2 every given time in accordance with the current signal c from the superposed signal applying section 10, and outputs the current measured data f representing the result of measurement to the measured data recording and predicting section 40.

The measured data recording and predicting section 40 comprises, for example, a personal computer, and records impedance measured data d, e from the impedance measuring section 20, and current measured data f from the current measuring section 30, followed by executing the calculation mentioned later of each data, and thereby, charge transfer resistance $R_{ct}$, surface static capacity C, and solution resistance $R_{sol}$ at oxide film formed on the metal layer surface are calculated, and the generation period of short circuit due to migration is predicted in accordance with the result of calculation.

Next, the prediction executed by the measured data recording and predicting section 40 is described in detail with reference to FIG. 1 and FIG. 4.

Figure 4:
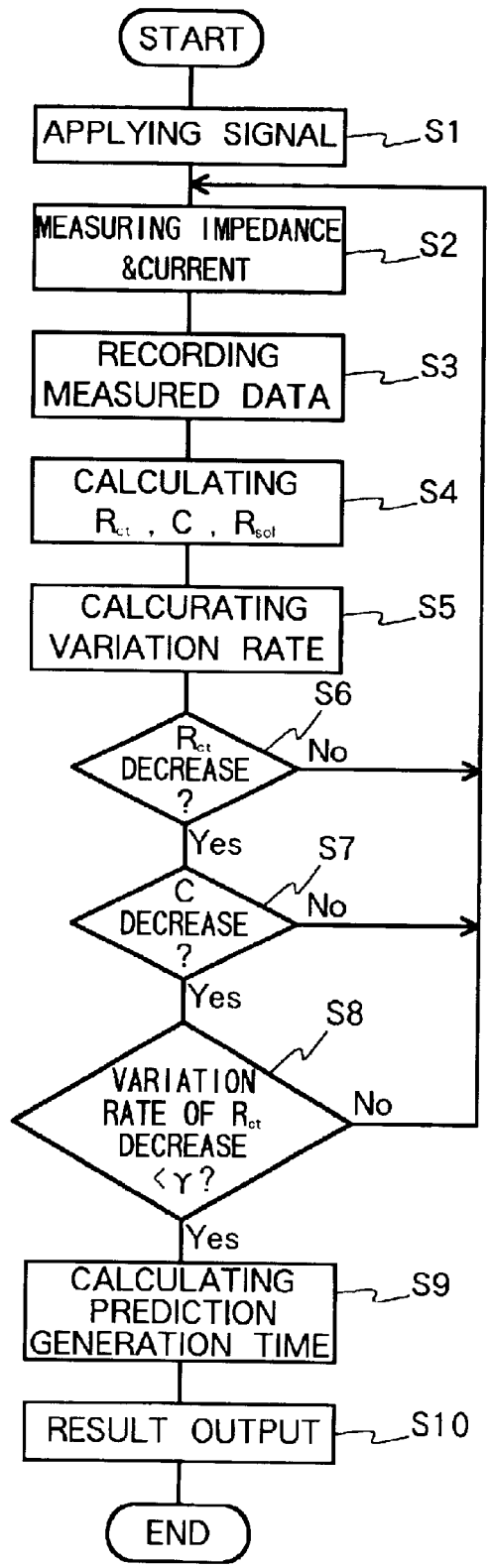
FIG. 4 is a flow chart of prediction procedures executed by a measured data recording and predicting section of the measuring apparatus.

The broken line in FIG. 1 stands for the control signal from the measured data recording and predicting section 40, and the numerals S1~S10 in FIG. 4 are the step numbers.

Step 1: Superposed signal a output from superposed signal applying section 10 is applied to electrodes 1, 2.

Step 2: Real number impedance measured data d, imaginary number impedance measured data e and current measured data f are subjected to sampling at predetermined intervals, for example, at 100 sec. intervals.

Step 3: The data sampled in the step 2 are recorded.

Step 4: Charge transfer resistance $R_{ct}$, surface static capacity C, and solution resistance $R_{sol}$ are calculated from each of the measured data d, e, f.

How to calculate the charge transfer resistance $R_{ct}$, surface static capacity C, and solution resistance $R_{sol}$ is described in the following with reference to FIG. 5.

Figure 5:
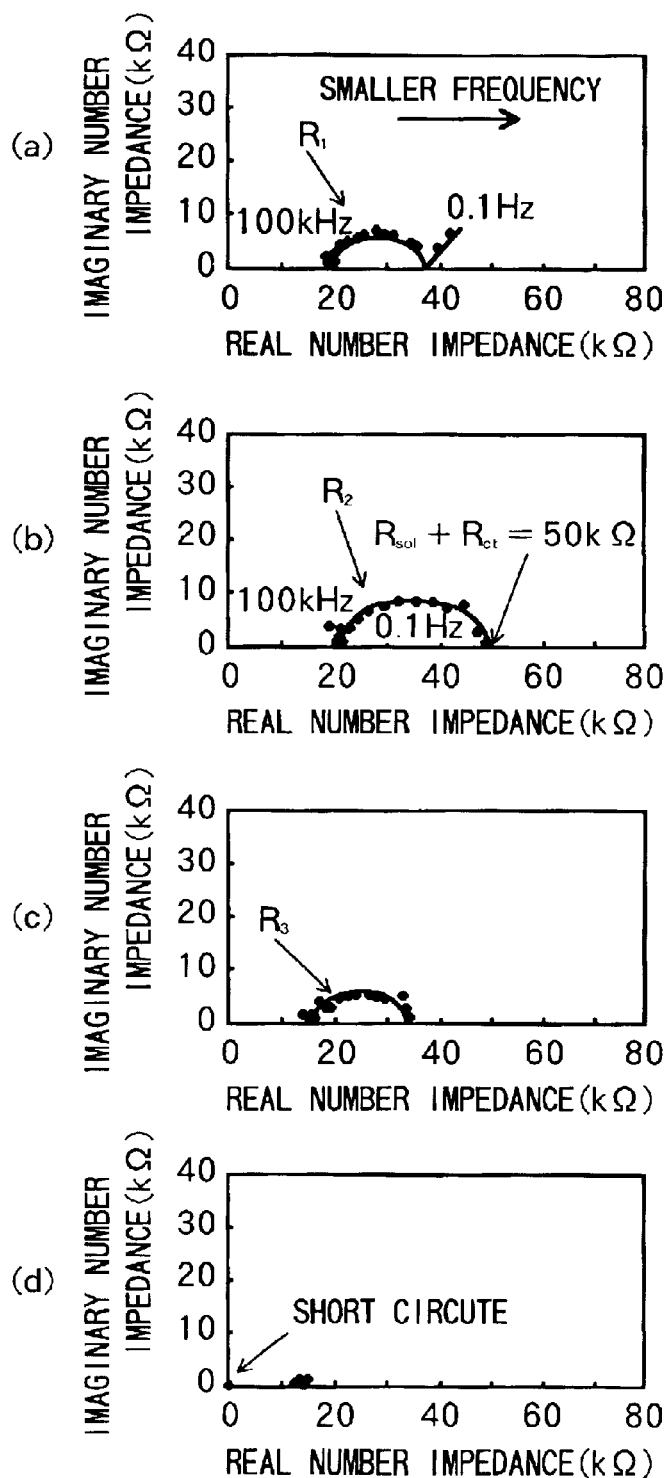
FIG. 5 is a complex plan view showing the principle of calculation of charge transfer resistance and surface static capacity.

FIG. 5 is a complex plan view, plotting the real number impedance measured data d (horizontal axis of each figure) and imaginary number impedance measured data e (vertical axis of each figure) corresponding to each frequency by changing the frequency of alternating current component of superposed signal a so as to be logarithmically swept to 100 kHz to 0.1 Hz in each stage of migration.

In the figure, drawn by the plotted points (d, e) are a locus in combination of semi-circular arc $R_1$ and straight line immediately after starting the measurement (see (a) in the figure), a locus of only semi-circular arc $R_2$ after lapse of a given time (300 sec. for example, see (b) in the figure) since the start of the measurement, and further, a locus of semi-circular arc $R_3$, smaller than the semi-circular arc $R_2$, at the time of generation of migration (500 sec. later for example, see (c) in the figure). And, when short circuit is generated between the electrodes (600 sec. later for example), both real number impedance (about 100 Ω) and imaginary number impedance are converged to a constant value.

Then, charge transfer resistance $R_{ct}$ is shown as the diameter of each arc $R_1$, $R_2$, $R_3$. Also, solution resistance $R_{sol}$ is shown as the value proximate to value 0 out of the two intersections of each semi-circular arc $R_1$, $R_2$, $R_3$ and horizontal axis.

Also, surface static capacity C is calculated by the following equation (1).

$$C=1/(2\pi \cdot F_{max} \cdot R_{ct}) \qquad (1)$$

where $F_{max}$ is the maximum frequency of data plotted at the peak of each semi-circular arc $R_1$, $R_2$, $R_3$.

Step 5: The variation rate $\epsilon_R$ of charge transfer resistance $R_{ct}$ is obtained. The variation rate $\epsilon_R$ (%) is calculated by the following equation (2).

$$\epsilon_R=((\text{measured value}-\text{previously measured value})/\text{previously measured value})\times 100 \qquad (2)$$

where the previously measured value is the data measured one time earlier than the data measured every measuring time.

Step 6: Whether or not the value of charge transfer resistance $R_{ct}$ is decreased is checked after lapse of a given time since the start of impedance measurement. Then, if there is rapid decrease in value of charge transfer resistance $R_{ct}$, that is, in case the decreasing speed of charge transfer resistance $R_{ct}$ is exceeding the threshold value, it will proceed to the next step 7, and contrarily, if there is no rapid decrease of charge transfer resistance $R_{ct}$, it will return to the step 2. Here, the given time is properly set according to the material quality of the electrode metal or the specimen.

Step 7: Whether or not the value of surface static capacity C is decreased is checked after lapse of a given time since the start of impedance measurement. Then, if there is rapid decrease in value of surface static capacity C, that is, in case the decreasing speed of static capacity C is exceeding the threshold value, it will proceed to the next step 8, and contrarily, if there is no rapid decrease of surface static capacity C, it will return to the step 2. Here, the given time is properly set according to the material quality of the electrode metal.

Step 8: Whether or not the variation rate $\epsilon_R$ of the value of charge transfer resistance $R_{ct}$ is smaller than threshold value $\gamma (\gamma<0)$ for inflection point detection is checked. Then, if the variation rate $\epsilon_R$ of charge transfer resistance $R_{ct}$ is smaller than the threshold value $\gamma$, that is, in case the variation rate $\epsilon_R$ of charge transfer resistance $R_{ct}$ is exceeding the threshold value $\gamma$ (namely if the inflection point is detected), it will proceed to the next step 9, predicting that short circuit between electrodes is generated after lapse of a given time, and contrarily, if the inflection point is not detected, it will return to the step 2.

That is, the generation of migration is closely related to the stability of oxide film usually formed on a metal layer surface, and if the oxide film is broken, it will accelerate the development of migration. Accordingly, previously obtained through experiment is the variation rate $\epsilon_R$ of charge transfer resistance $R_{ct}$ at start of rapid progress of migration, and then the threshold value $\gamma$ for inflection point detection is set with reference to the result obtained. Regarding the setting of threshold value $\gamma$ for inflection point detection, the detail will be later described in the description of examples.

Step 9: The calculation for short-circuit generation time prediction is executed for predicting the time until generation of short circuit between electrodes due to migration, and short-circuit generation predicted time $T_E$ (sec. or hours) is calculated by the following equation (3).

$$T_E=T_D+(R_{ctD}/(R_{ctB}-R_{ctD}))^{0.5} \times T_S \qquad (3)$$

where $T_D$: time until inflection point detection in step 8 [sec. or hours]

$T_{ctB}$: charge transfer resistance before inflection point detection [kΩ]

$R_{ctD}$: charge transfer resistance at inflection point detection [kΩ]

$T_S$: measuring time interval [sec. or hours]

Step 10: The result of prediction, that is, short circuit generation predicted time $T_F$ is output.

Thus, according to the first embodiment, since migration is measured by using the decrease of surface static capacity C and the decrease of charge transfer resistance $R_{ct}$, it is possible to precisely grasp the process of migration in real time or on-line. Also, according this first embodiment, short-circuit generation predicted time $T_E$ can also be obtained by the above equation (3), and as a result, it is possible to shorten the product evaluation period, resulting in improvement of the productivity.

Embodiment 2

The second embodiment of the present invention will be described with reference to FIG. 6 and FIG. 7. In the second embodiment, migration is measured in a steam atmosphere instead of the measuring method using ion-exchanged water 4 (hereinafter referred to as water drop method) in the first embodiment. In other words, migration is measured by an environmental test method (or humidity test method).

FIG. 6(a) shows a state of voltage distribution across electrodes 1, 2 in the environmental test method in the second embodiment. FIG. 7(a) shows a state of voltage distribution across electrodes 1, 2 in the water drop method in the first embodiment for the purpose of comparison. Also, (b) in each figure stands for equivalent circuit. In the figures, the numerals $C1_{eq}$, $C2_{eq}$ are respectively the equivalent surface static capacities of anode and cathode, $R_{ct1eq}$, $R_{ct2eq}$ are respectively the equivalent charge transfer resistance of anode and cathode, and $R_{soleq}$ is the equivalent solution resistance.

As shown in FIG. 7, since the quantity of water is adequate in the migration measurement using ion exchanged water 4, solution resistance component $R_{sol}$ becomes constant readily (within 10 sec.) after starting the measurement, and the value (about 2 kΩ) is small enough as compared with charge transfer resistance $R_{ct}$ and surface static capacity C (C1, C2). Therefore, taking into account the value of $R_{sol}$ is of little necessity for the evaluation of migration.

On the other hand, in the environmental test method, since water content is given in the form of steam, it takes 100 hours or more until moisture absorption by the specimen is made as shown in FIG. 6. Also, the quantity of water content is small, and the value of solution resistance $R_{sol}$ becomes relatively large (about 30 kΩ), and moreover, the value also changes with the lapse of time. Therefore, for the migration measurement by the environmental test method, it is necessary to grasp the patterns of change with time of surface static capacity C, charge transfer resistance $R_{ct}$, solution resistance $R_{sol}$, and current.

Figure 8:
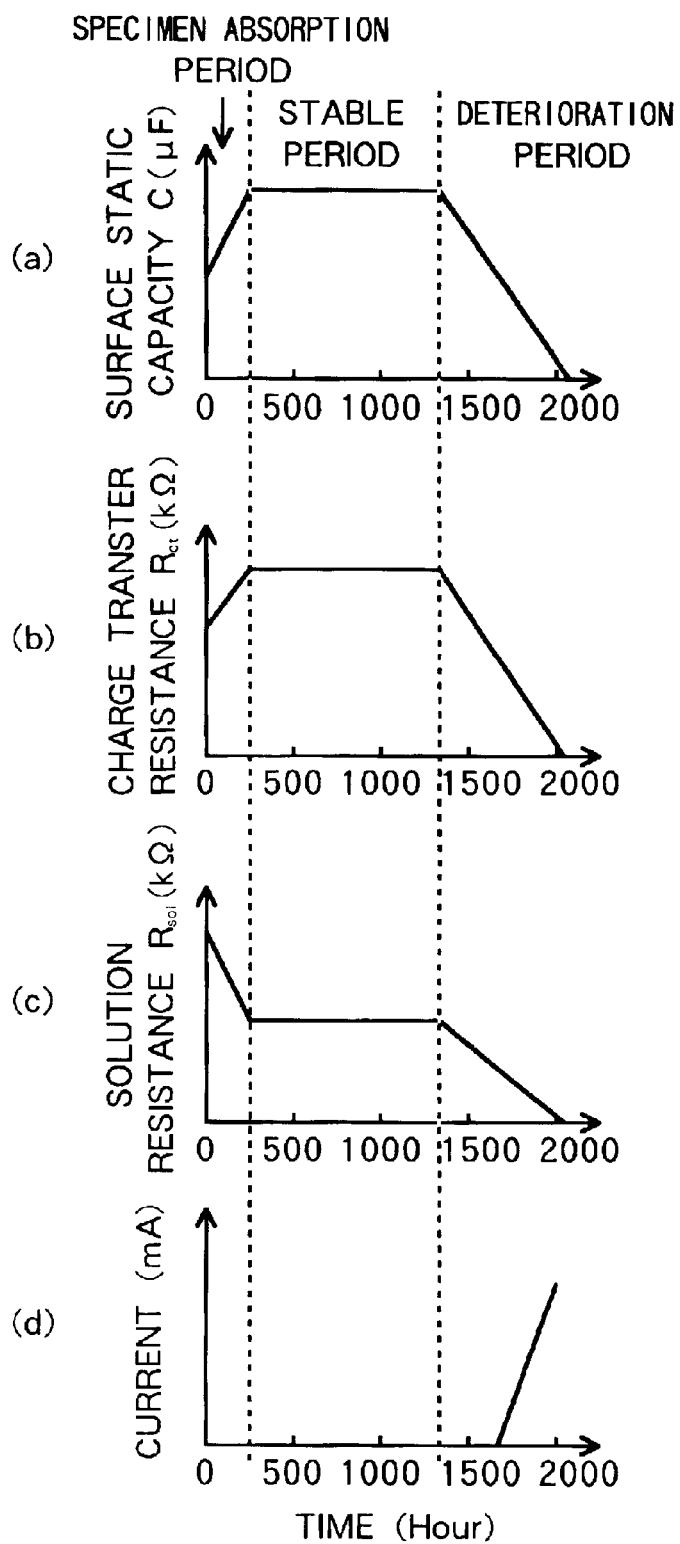
FIG. 8 includes graphs schematically showing characteristic changes in the second preferred embodiment of the present invention.

Shown in FIG. 8 are schematic diagrams of changes with time of surface static capacity C [(a) in the figure], charge transfer resistance $R_{ct}$ [(b) in the figure], solution resistance $R_{sol}$ [(c) in the figure], and current [(d) in the figure] in the environmental test method.

As shown in FIG. 8, during the period of moisture absorption by the specimen (specifically, about 100 hours after starting the measurement), the solution resistance $R_{sol}$ is decreased as moisture being absorbed by the specimen. Also, due to the decrease of solution resistance $R_{sol}$, the voltage applied to the electrode surface is increased, therefore the surface static capacity C and charge transfer resistance $R_{ct}$ are increased.

With the lapse of the period of moisture absorption by the specimen, the values of surface static capacity C, charge transfer resistance $R_{ct}$, and solution resistance $R_{sol}$ are maintained constant, entering into a stable period.

At the end of the stable period, surface static capacity C and charge transfer resistance $R_{ct}$ begin to decrease as the electrode surface film being broken. That is, it causes generation of inflection point. In this case, since solution resistance $R_{sol}$ is larger as compared with the value in a water drop method, the migration reaction of metal ion does not go on rapidly. Therefore, the surface static capacity C and charge transfer resistance $R_{ct}$ are slowly decreased.

Also, predicted time (short circuit generation predicted time) $T_E$ (sec. or hours) until generation of short-circuit between electrodes due to migration is calculated by the following equation (4).

$$T_E = T_D + (R_{cte}/(R_{cte} - R_{ctd}))^{0.5} \times ((R_{cte} + R_{sol})/R_{cte})^2 \times T_S \quad (4)$$

where $T_D$: time until inflection point detection [sec. or hours]

$R_{cte}$: charge transfer resistance before inflection point detection (charge transfer resistance in stable period) [kΩ]

$R_{ctd}$: charge transfer resistance at inflection point detection [kΩ]

$R_{sol}$: solution resistance before inflection point detection [kΩ]

$T_S$: measuring time interval [sec. or hours]

The short-circuit generation predicted time $T_E$ of a certain specimen calculated by the equation (4) was 2,800 hours. Also, the actual short-circuit generation time of the specimen was about 3,000 hours. Therefore, it is clear that the short-circuit generation predicted time $T_E$ calculated by the equation (4) generally matches the actual short-circuit generation time. Also, the inflection point detection time in this specimen was 1,000 hours after starting the measurement. Therefore, it is possible to make the prediction of short-circuit generation about 2,000 hours earlier in the above example.

As for the other specimens, similar results have been obtained through similar prediction although there are some variations.

Thus, according to the equation (4), it is possible to know the generation period of short circuit between electrodes due to migration in the environmental test method thousands of hours earlier. As a result, the evaluation period of migration resistance of the product is greatly shortened resulting in improvement of the productivity.

The present invention will be more specifically described in the following according to the examples.

EXAMPLES 1 TO 3 AND COMPARATIVE EXAMPLES 1 TO 3

In the measuring apparatus K of the first embodiment, the anode 1 used is a solder plated tin bar (99.0% purity) of 3.0 mm in diameter, and the cathode 2 is an electrode (electrode area: 1.37 cm$^2$) formed by evaporating Au on AT cut crystal (resonant frequency: 5 MHz). And, various metal layers were formed on the surface of each electrode 1, 2, and the migration evaluation test was executed under the following conditions (examples 1 to 3).

Also, besides the examples 1 to 3, the results of migration evaluation tests executed by QCM method are shown as comparative examples 1 to 3. The test conditions are as follows:

Gap between electrodes: 0.3 mm, volume of ion-exchanged water: 1 mL, DC component of AC signal: 1.5V, AC signal voltage: 50 mV.

Example 1, comparative example 1: Sn–3.5 Ag (melting point: 221° C.)

Example 2, comparative example 2: Sn–9 Zn (melting point: 198.5° C.)

Example 3, comparative example 3: Sn–37 Pb (melting point: 183.3° C.)

Figure 9:
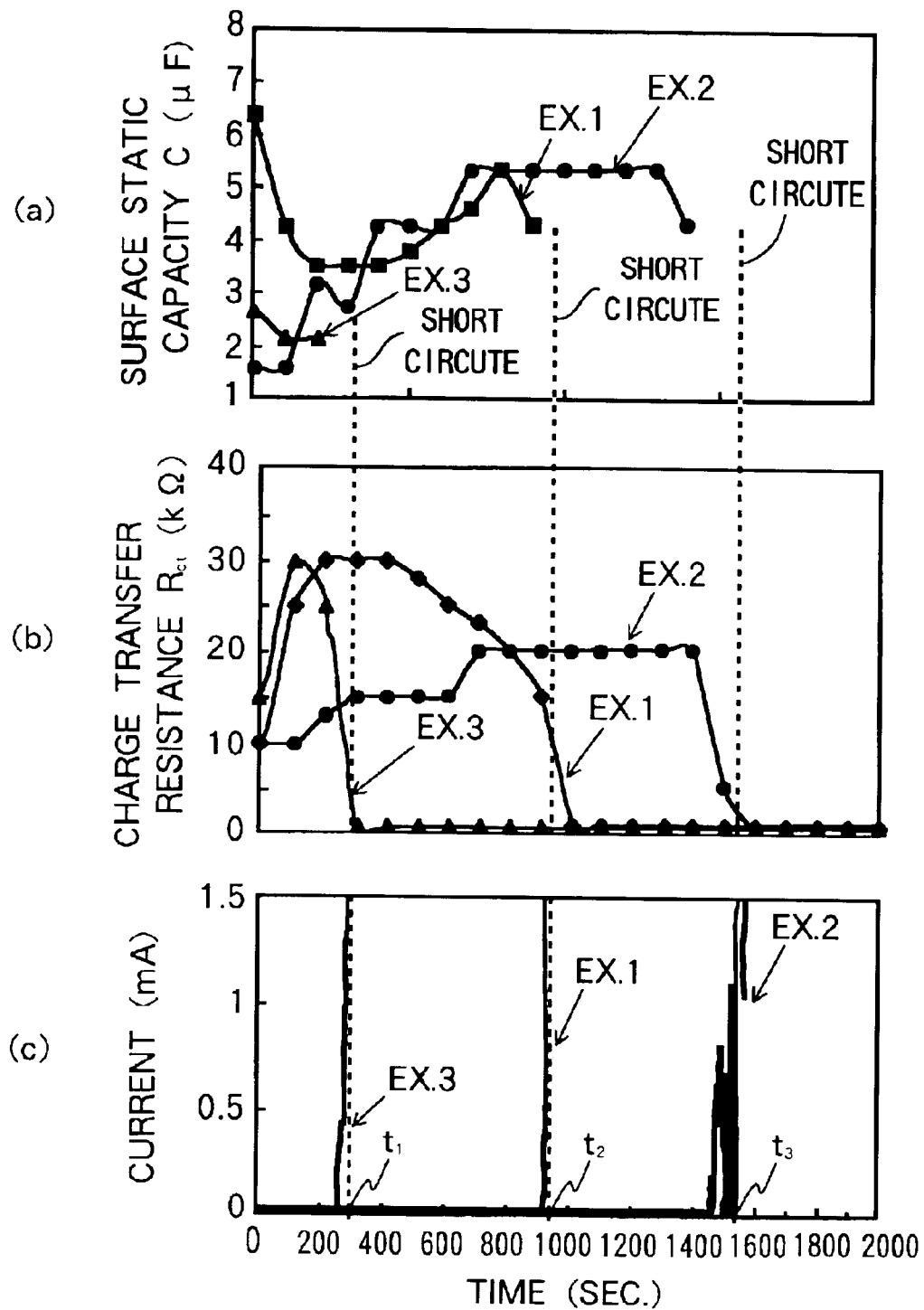
FIG. 9 includes graphs showing the changes of various electrical information in the examples 1 to 3.
Figure 10:
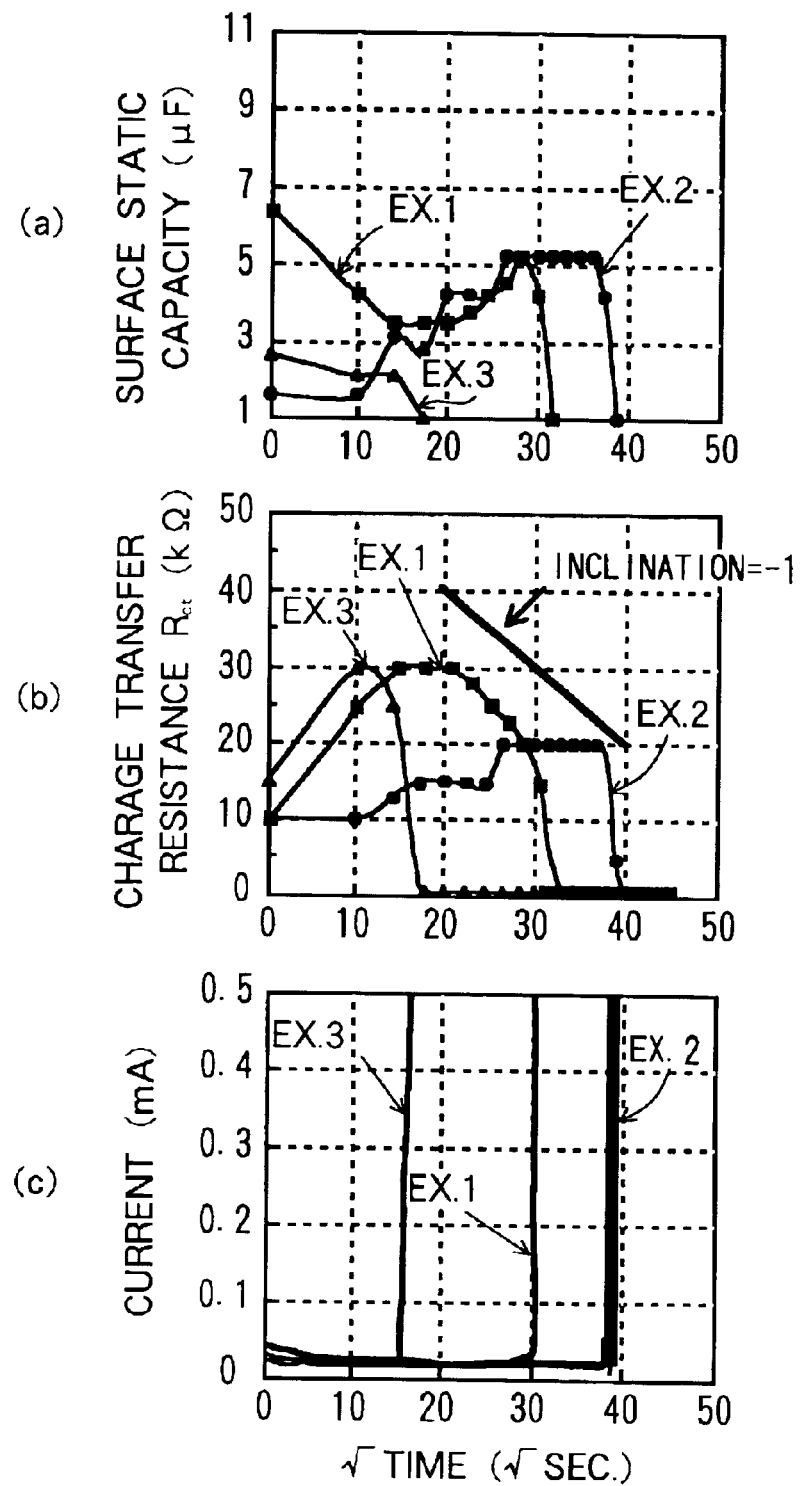
FIG. 10 includes graphs same as FIG. 9 except that the horizontal axis is the square root of lapsed time.
Figure 11:
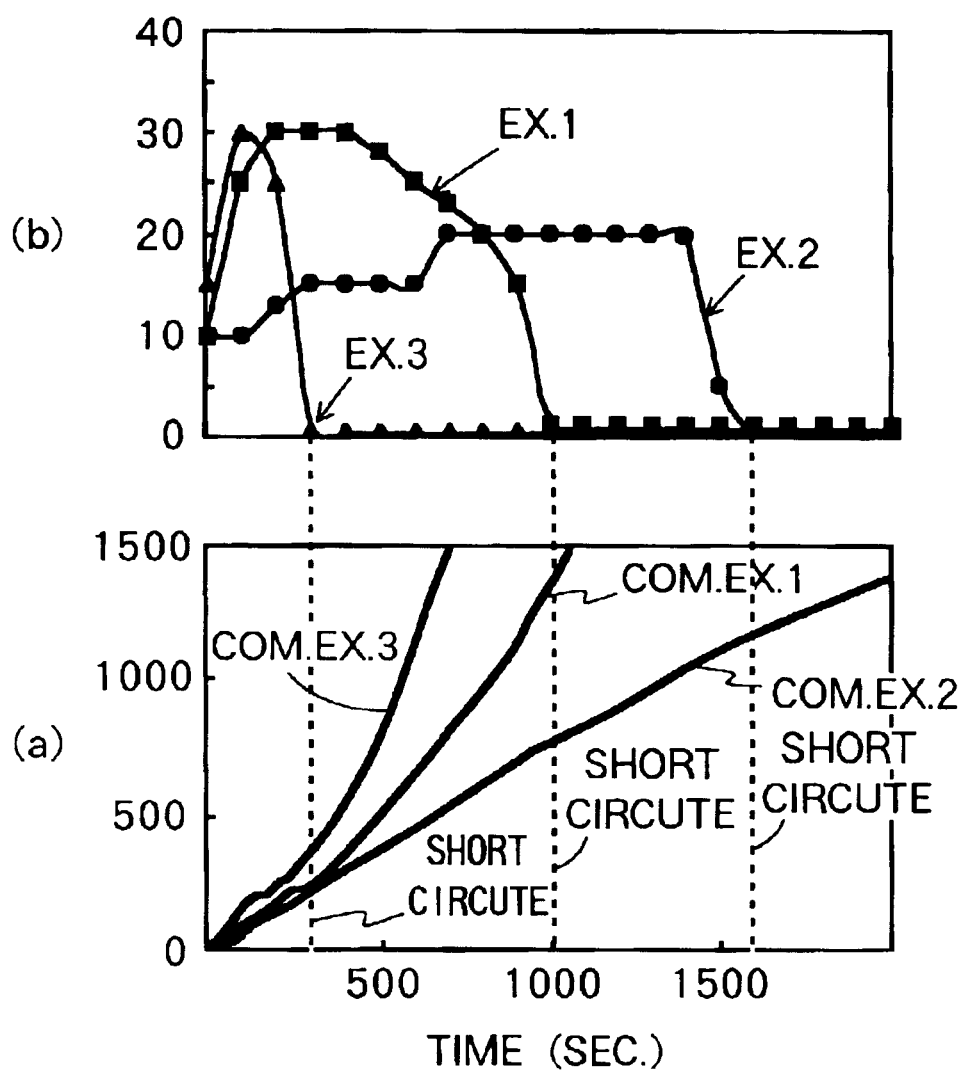
FIG. 11 includes graphs showing the changes of resonant frequency in the comparative examples 1 to 3 in comparison with the changes of charge transfer resistance in the examples 1 to 3.

FIG. 9 shows the changes of surface static capacity C [(a) in the figure], charge transfer resistance $R_{ct}$ [(b) in the figure], and current value [current measured data f, (c) in the figure] after start of the measurement in examples 1 to 3. FIG. 10 shows diagrams same as FIG. 9 except that the horizontal axis is the square root of lapsed time. FIG. 11 shows the resonant frequency changes [(a) in the figure] of AT cut crystal in comparative examples 1 to 3 in comparison with the variations of charge transfer resistance $R_{ct}$ [(b) in the figure] in examples 1 to 3.

Figure 12:
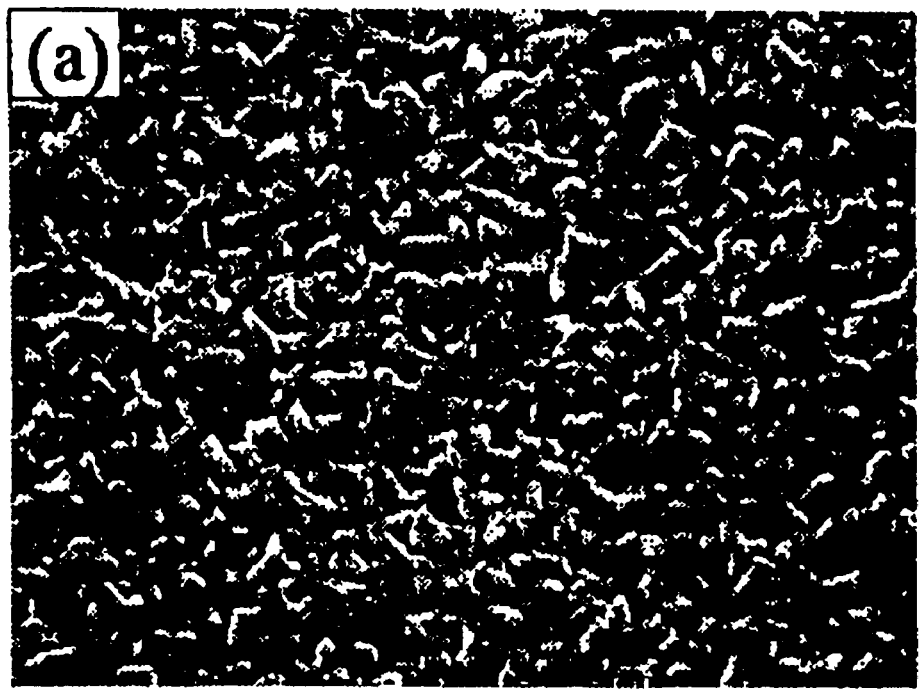
FIG. 12 is a photo of a cathode surface in the first example, taken by a scanning electron microscope, showing a status before start of the test.
Figure 15:
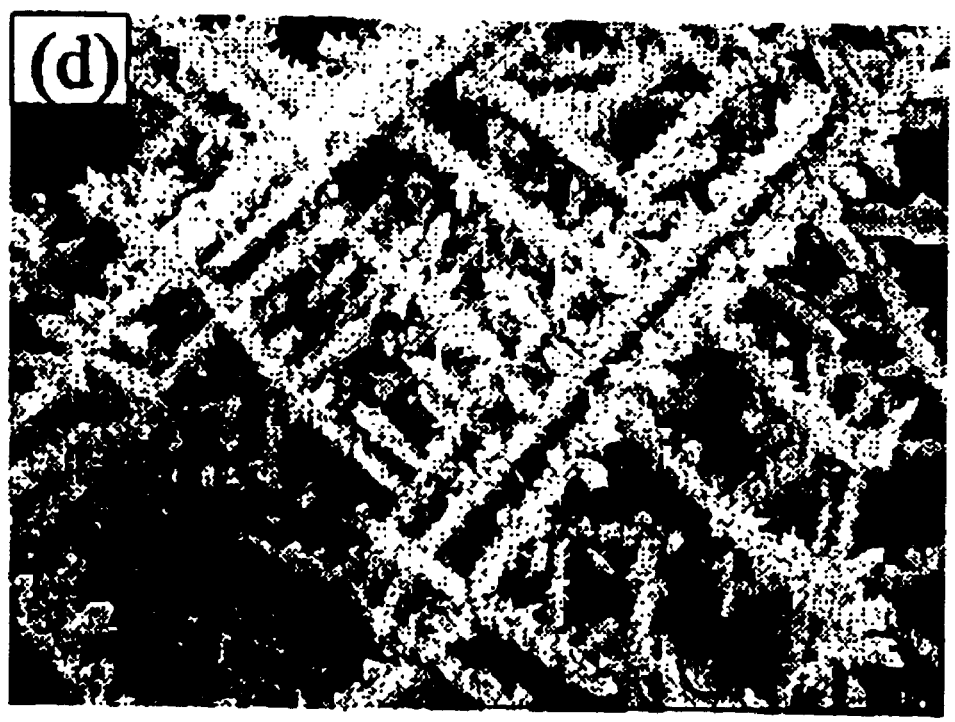
FIG. 15 is a photo of a cathode surface in the first example, taken by a scanning electron microscope, showing a status 1,000 seconds after start of the test.

Also, FIG. 12 shows the result of before-test observation by a scanning electron microscope of the cathode surface of example 1. FIG. 13 shows the result of observation before short circuit between electrodes by a scanning electron microscope of the cathode surface of example 1. FIG. 14 shows the result of observation immediately after short circuit between electrodes by a scanning electron microscope of the cathode surface of example 1. FIG. 15 shows the result of observation after a lapse of 1,000 sec. from starting the measurement by a scanning electron microscope of the cathode surface of example 1.

From FIG. 9 and FIG. 10, in the examples 1 to 3, it has been confirmed that just before time $t_1$, $t_2$, $t_3$ of generation of short circuit between electrodes [(c) in each figure], surface static capacity C first decreases rapidly [see (a) in each figure], followed by rapid decrease of charge transfer resistance $R_{ct}$ [(b) in each figure], leading to short circuit between electrodes. Here, it is preferable to set the threshold value γ for inflection point detection of embodiment 1 to a rate of change that matches the inclination (−1) in FIG. 10.

Also, from FIG. 11, in the migration evaluation test based on the QCM method [comparative examples 1 to 3, (a) in the figure], as compared with the examples 1 to 3 based on the AC impedance method, it is more difficult to precisely detect the time $t_1$, $t_2$, $t_3$ of generation of short circuit between electrodes in accordance with the change of resonant frequency.

Further, from FIG. 12 to FIG. 15, it can be confirmed that the electrode surface is entirely covered with fine migration, before start of short circuit between electrodes (see FIG. 13), and that branched migrations are generated toward the counter electrode, just after generation of short circuit (see FIG. 14), and that a number of branched migrations are growing, 1,000 seconds after starting the test (see FIG. 15).

Also, regarding the examples 1 to 3, the short-circuit generation predicted time was calculated from the equation (3). As a result, the time was 1,100 sec. in the example 1, 1,615 sec. in the example 2, and 275 sec. in the example 3. Since these results match the measuring results shown in FIG. 9, it can be said that the equation (3) enables the accurate prediction of short-circuit generation.

The present invention has been described above in accordance with the embodiments and examples. However, the present invention is not limited to these embodiments and examples, but it is possible to include various remodeling or improvements. For example, in the embodiment, surface static capacity and charge transfer resistance are used to grasp the process of migration, but it is also possible to grasp the process of migration by using only either one of surface static capacity or charge transfer resistance. Also, it is possible to make the electrodes various in shape, for example, parallel electrodes.

As described above, the present invention brings about excellent advantages such as it is able to accurately measure the process of migration in real time or on-line.

Also, according to the embodiment of the present invention, the time until generation of short circuit between electrodes due to migration can be predicted, and therefore, it is possible to considerably shorten the time required for the evaluation of migration resistance and to obtain excellent advantages such as remarkable improvement of the productivity.

We claim:

1. A migration measuring method based on an alternating current impedance method, wherein direct current with fine alternating current superposed is applied across electrodes to measure the impedance therebetween, and then a surface static capacity is calculated from the measured value of impedance in order to measure migration in accordance with the variation of the calculated surface static capacity.

2. The migration measuring method of claim 1, wherein generation of migration is detected by rapid decrease of surface static capacity after lapse of a given time since the start of impedance measurement.

3. A migration measuring method based on an alternating current impedance method, wherein direct current with fine alternating current superposed is applied across electrodes to measure the impedance therebetween, and then a charge transfer resistance is calculated from the measured value of impedance in order to measure migration in accordance with the variation of the calculated charge transfer resistance.

4. The migration measuring method of claim 3, wherein generation of migration is detected by detecting rapid decrease of charge transfer resistance after lapse of a given time since the start of impedance measurement.

5. A migration measuring method based on an alternating current impedance method, wherein direct current with fine alternating current superposed is applied across electrodes to measure the impedance therebetweeen, and then a surface static capacity and a charge transfer resistance are calculated from the measured value of impedance in order to measure the migration in accordance with the variation of the calculated surface static capacity and charge transfer resistance.

6. The migration measuring method of claim 5, wherein generation of migration is detected by detecting rapid decrease of surface static capacity and charge transfer resistance after lapse of a given time since the start of impedance measurement.

7. The short-circuit generation time predicting method based on an alternating current impedance method for predicting the generation time of short circuit between electrodes due to migration, wherein direct current with fine alternating current superposed is applied across electrodes to measure the impedance threrebetween, and then a charge transfer resistance is calculated from the measured value of impedance in order to measure the generation time of short circuit due to migration in accordance with the calculated charge transfer resistance.

8. The short-circuit generation time predicting method of claim 7, wherein short-circuit generation predicted time is calculated by the following equation when a water drop method is applied, $$T_E = T_D + (R_{ctB}/(R_{ctB} - R_{ctD}))^{0.5} \times T_S$$

where $T_E$: short-circuit generation predicted time $T_D$: time until inflection point detection $R_{ctB}$: charge transfer resistance before inflection point detection $R_{ctD}$: charge transfer resistance at inflection point detection $T_S$: measuring time interval.

9. The short-circuit generation time predicting method of claim 7, wherein the short-circuit generation predicted time is calculated by the following equation when an environmental test method or a humidity test method is applied, $$T_E = T_D + (R_{cte}/(R_{cte} - R_{ctd}))^{0.5} \times ((R_{cte} + R_{sol})/Rc_{tc})^2 \times T_S$$

where $T_E$: short-circuit generation predicted time $T_D$: time until inflection point detection $R_{cte}$: charge transfer resistance before inflection point detection $R_{ctd}$: charge transfer resistance at inflection point detection $R_{sol}$: solution resistance before inflection point detection $T_S$: measuring time interval.

10. The measuring method of claim 1, 2, 3, 4, 5, 6, 7, 8 or 9, wherein an anode is a bar-shaped electrode, and a cathode is a flat-plate electrode.

11. A migration measuring apparatus using an alternating current impedance method, comprising: a superposed signal applying section for applying direct current with fine alternating current superposed across electrodes; a current measuring section; an impedance measuring section for measuring impedance between electrodes; and a measured data recording and processing section for recording and processing the value measured by said impedance measuring section in order to measure migration, wherein said measured data recording and processing section calculates a surface static capacity from the measured value of impedance and measures migration in accordance with the variation of the calculated surface static capacity.

12. The migration measuring apparatus of claim 11, wherein said measured data recording and processing section detects the generation of migration by detecting rapid decrease of surface static capacity after lapse of a given time since the start of impedance measurement.

13. A migration measuring apparatus using an alternating current impedance method, comprising: a superposed signal applying section for applying direct current with fine alternating current superposed across electrodes; a current measuring section; an impedance measuring section for measuring impedance between electrodes; and a measured data recording and processing section for recording and processing the value measured by said impedance measuring section in order to measure migration, wherein said measured data recording and processing section calculates charge transfer resistance from the measured value of impedance and detects the generation of migration in accordance with the variation of the calculated charge transfer resistance.

14. The migration measuring apparatus of claim 13, wherein said measured data recording and processing section detects the generation of migration by detecting rapid decrease of charge transfer resistance after lapse of a given time since the start of impedance measurement.

15. A migration measuring apparatus using an alternating current impedance method, comprising: a superposed signal applying section for applying direct current with fine alternating current superposed across electrodes; a current measuring section; an impedance measuring section for measuring impedance between electrodes; and a measured data recording and processing section for recording and processing the value measured by said impedance measuring section in order to measure migration, wherein said measured data recording and processing section calculates a surface static capacity and a charge transfer resistance from the measured value of impedance and measures the generation of migration in accordance with the variation of calculated surface static capacity and charge transfer resistance.

16. The migration measuring apparatus of claim 15, wherein said measured data recording and processing section detects the generation of migration by detecting rapid decrease of surface static capacity and charge transfer resistance after lapse of a given time since the start of impedance measurement.

17. A short-circuit generation time predicting apparatus using an alternating current impedance method for predicting the generation time of short circuit between electrodes due to migration, comprising: a superposed signal applying section for applying direct current with fine alternating current superposed across electrodes; a current measuring section; an impedance measuring section for measuring impedance between electrodes; and a measured data recording and predicting section for recording the value measured by said impedance measuring section and predicting the generation time of short circuit between electrodes due to migration, wherein a charge transfer resistance is calculated from the measured value of impedance, and the generation time of short circuit due to migration is predicted in accordance with the calculated charge transfer resistance.

18. The short circuit generation time predicting apparatus of claim 17, wherein short-circuit generation predicted time is calculated by the following equation when a water drop method is applied, $$T_E = T_D + (R_{ctB}/(R_{ctB}-R_{ctD}))^{0.5} \times T_S$$

where $T_E$: short-circuit generation predicted time $T_D$: time until inflection point detection $R_{ctB}$: charge transfer resistance before inflection point detection $R_{ctD}$: charge transfer resistance at inflection point detection $T_S$: measuring time interval.

19. The short-circuit generation time predicting apparatus of claim 17, wherein the short-circuit generation predicted time is calculated by the following equation when an environmental test method or humidity test method is applied, $$T_E = T_D + (R_{cte}/(R_{cte}-R_{ctd}))^{0.5} \times ((R_{cte}+R_{sol})/R_{cte})^2 \times T_S$$

where $T_E$: short-circuit generation predicted time $T_D$: time until inflection point detection $T_{cte}$: charge transfer resistance before inflection point detection $R_{ctd}$: charge transfer resistance at inflection point detection $R_{sol}$: solution resistance before inflection point detection $T_S$: measuring time interval.

20. The apparatus of claim 11, 12, 13, 14, 15, 16, 17, 18 or 19, wherein an anode is a bar-shaped electrode, and a cathode is a flat-plate electrode.

* * * * *